United States Patent
Vertoprakhov et al.

(10) Patent No.: US 9,824,432 B2
(45) Date of Patent: Nov. 21, 2017

(54) PERIPHERAL INSPECTION SYSTEM AND METHOD

(71) Applicant: MICROVIEW TECHNOLOGIES PTE LTD, Singapore (SG)

(72) Inventors: Victor Vertoprakhov, Novosibirsk (RU); Wong Soon Wei, Singapore (SG); Sergey Smorgon, Krasniyarsk (RU)

(73) Assignee: MICROVIEW TECHNOLOGIES PTE LTD, Singapore (SG)

( * ) Notice: Subject to any disclaimer, the term of this patent is extended or adjusted under 35 U.S.C. 154(b) by 374 days.

(21) Appl. No.: 14/445,010

(22) Filed: Jul. 28, 2014

(65) Prior Publication Data

US 2014/0333760 A1    Nov. 13, 2014

Related U.S. Application Data

(63) Continuation of application No. 11/484,282, filed on Jul. 11, 2006, now abandoned.

(51) Int. Cl.
*G06K 9/00* (2006.01)
*G06T 7/00* (2017.01)
(Continued)

(52) U.S. Cl.
CPC ....... *G06T 7/0004* (2013.01); *G01N 21/8803* (2013.01); *G01N 21/8806* (2013.01);
(Continued)

(58) Field of Classification Search
None
See application file for complete search history.

(56) References Cited

U.S. PATENT DOCUMENTS

| 4,435,641 A | 3/1984 | Hajime |
| 4,454,542 A | 6/1984 | Miyazawa |

(Continued)

FOREIGN PATENT DOCUMENTS

| CN | 1111351 A | 11/1995 |
| CN | 1222280 A | 7/1999 |

(Continued)

OTHER PUBLICATIONS

Nayar et al., "Folded Catadioptric Cameras", IEEE CVPR'99, vol. 2, (Jun 23-25, 1999), pp. 217-223.*

(Continued)

*Primary Examiner* — Manuchehr Rahmjoo
(74) *Attorney, Agent, or Firm* — Jackson Walker LLP; Christopher J. Rourk

(57) ABSTRACT

A method of inspecting two or more sides of an object is provided. The method includes generating one set of image data of two or more sides of the object, such as by using spherical mirror segments that project all sides of the object onto a single image and generating an X by Y array of image data of the single image. The projection of the image data is then compensated for, such as by identifying inspection processes to locate defects of the object in the projected image data or by converting the image data from the projected inspection coordinates to Cartesian coordinates. Predetermined inspection processes are then performed on the compensated image data, such as by using the inspection processes that are optimized for use with the projected image data or by converting the projected image data into a Cartesian format and using Cartesian image data inspection processes.

20 Claims, 10 Drawing Sheets

(51) Int. Cl.
*G01N 21/88* (2006.01)
*G01N 21/952* (2006.01)
*G06T 3/00* (2006.01)
*G06T 5/00* (2006.01)

(52) U.S. Cl.
CPC ......... *G01N 21/952* (2013.01); *G06T 3/0043* (2013.01); *G06T 5/006* (2013.01); *G06T 2207/30108* (2013.01); *G06T 2207/30164* (2013.01)

(56) References Cited

U.S. PATENT DOCUMENTS

| | | | | |
|---|---|---|---|---|
| 4,697,076 A | * | 9/1987 | Yoshida | G01N 21/9054 209/526 |
| 4,758,084 A | * | 7/1988 | Tokumi | G01N 21/9054 250/223 B |
| 4,959,538 A | * | 9/1990 | Swart | G01N 21/9054 250/223 B |
| 5,030,823 A | * | 7/1991 | Obdeijn | G01N 21/909 250/223 B |
| 5,045,688 A | * | 9/1991 | Domenico | G01N 21/9054 250/223 B |
| 5,592,286 A | * | 1/1997 | Fedor | G01N 21/9054 250/223 B |
| 5,661,294 A | * | 8/1997 | Buchmann | G01N 21/9054 209/526 |
| 2003/0081952 A1 | | 5/2003 | Geng | |
| 2004/0105597 A1 | | 6/2004 | Lelescu et al. | |

FOREIGN PATENT DOCUMENTS

| | | |
|---|---|---|
| EP | 0047936 A1 | 3/1982 |
| EP | 0657732 A1 | 6/1995 |
| EP | 1061358 A2 | 12/2000 |
| EP | 1494010 A1 | 1/2005 |

OTHER PUBLICATIONS

Wikipedia, "Camera lens", Jul. 6, 2006 (archieved), http://en.wikipedia.org/wiki/Camera_lens, last accessed Jul. 24, 2016.*
The Search Report and Written Opinion forwarded by the Intellectual Property Office of Singapore dated Apr. 1, 2010 and ssued by the Austrian Patent Office Service and Information Center dated Feb. 25, 2010 for the co-pending Singapore patent application No. 200705154-3.
The Search and Examination Report issued by the Intellectual Property Office of Singapore dated Mar. 23, 2011 for the co-pending Singapore patent application No. 200705154-3.
The Office Action issued by the Taiwanese Patent Office dated Jun. 2, 2010 for the co-pending Taiwanese patent application No. 096125224.
The Communication issued by the European Patent Office dated Nov. 11, 2009 for co-pending European patent application No. 07013487.9.
The Communication issued by the European Patent Office dated Feb. 10, 2016 for co-pending patent application No. 07013487.9.
The Communication issued by the European Patent Office dated Jul. 4, 2016 for co-pending European patent application No. 07013487.9.
The Office Action issued by the State Intellectual Property Office of the P.R.C. dated Aug. 24, 210 for the co-pending Chinese patent application No. 200710136877.3

* cited by examiner

FIGURE 1    100

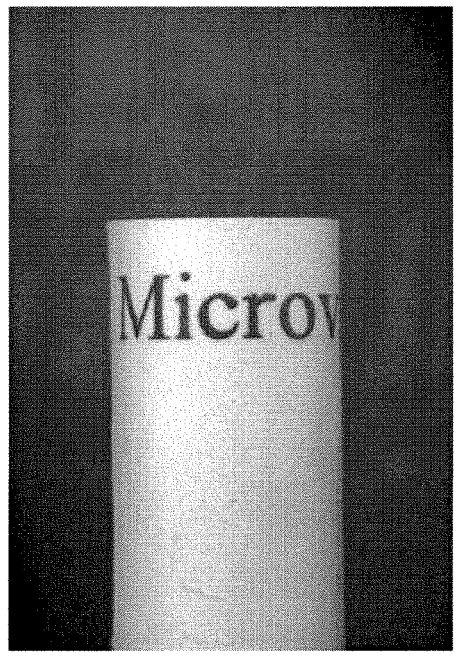
FIGURE 5A  500A ⇧
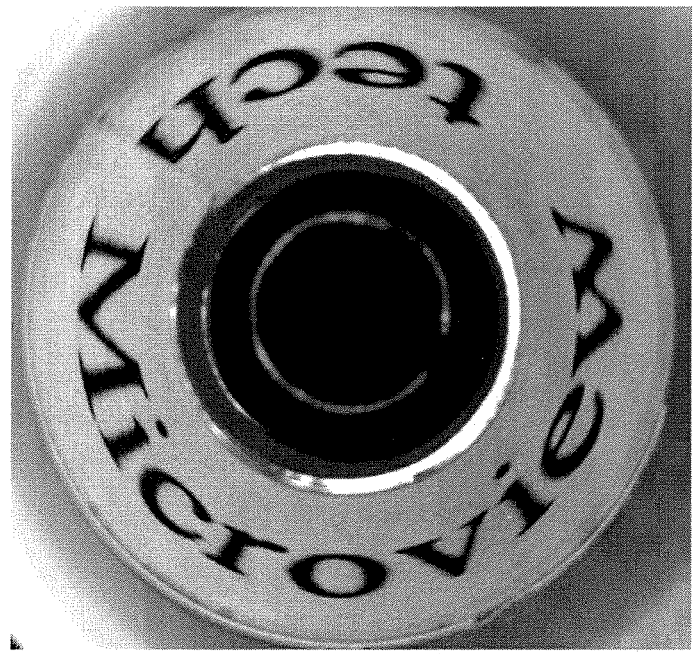
FIGURE 5B  500B ⇧

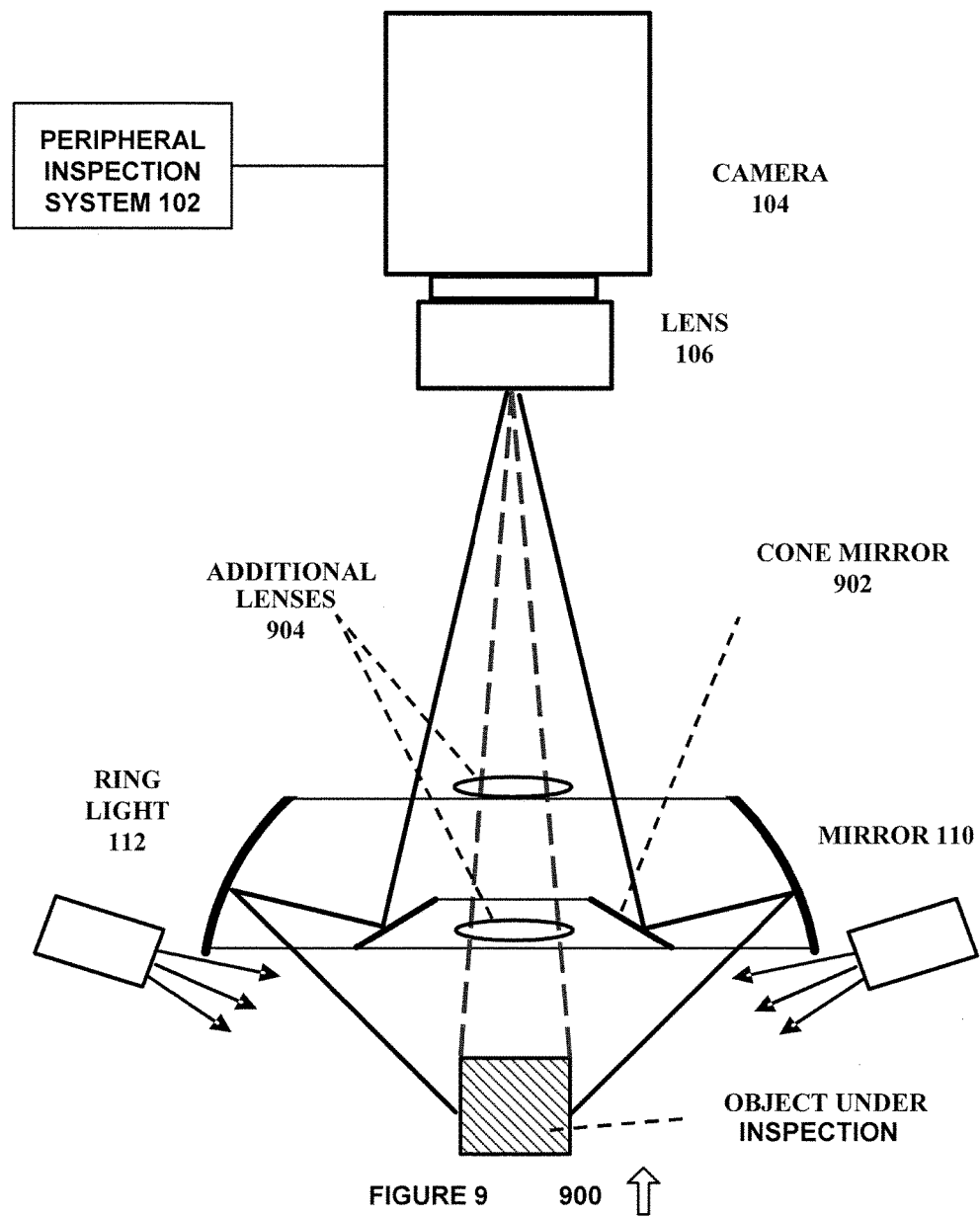

PERIPHERAL INSPECTION SYSTEM AND METHOD

FIELD OF THE INVENTION

The invention relates to optical inspection of objects to determine whether they meet required manufacturing specifications, and in particular to the optical inspection of the periphery of an object using a single set of image data.

BACKGROUND OF THE INVENTION

It is known to optically inspect manufactured items for defects that would render the item unusable. For objects have multiple surfaces, such as bolts or other items having a 3D continuous periphery, inspection typically requires obtaining multiple sets of image data. For example, such objects may be initially oriented in a predetermined position and then moved to other pre-determined positions. This requires multiple images of the object to be generated. Furthermore, the inspection system must still track the object and recognise it once it has reached the new orientation. This process requires a computationally intensive operation that can be the limiting factor in the production and quality control of objects.

SUMMARY OF THE INVENTION

In accordance with the present invention, a system and method for inspecting objects are provided that overcome known problems with systems and methods for inspecting objects.

In particular, a system and method for inspecting objects are provided which utilize a single set of image data that captures two or more sides of the object, such as image data of the entire periphery of the object in projected polar coordinates.

In accordance with an exemplary embodiment of the present invention, a method of inspecting two or more sides of an object is provided. The method includes generating one set of image data of two or more sides of the object, such as by using spherical mirror segments that project all sides of the object onto a single image and generating an X by Y array of image data of the single image. The projection of the image data is then compensated for, such as by identifying inspection processes to locate defects of the object in the projected image data or by converting the image data from the projected inspection coordinates to Cartesian coordinates. Predetermined inspection processes are then performed on the compensated image data, such as by using the inspection processes that are optimised for use with the projected image data or by converting the projected image data into a Cartesian format and using Cartesian image data inspection processes.

The present invention provides many important technical advantages. One important technical advantage of the present invention is an inspection system that utilizes a single image of an object under inspection, where spherical or conical mirrors are used to present a circumferential image of the sides of the object, so as to eliminate the need to obtain multiple images.

Those skilled in the art will further appreciate the advantages and superior features of the invention together with other important aspects thereof on reading the detailed description that follows in conjunction with the drawings.

BRIEF DESCRIPTION OF THE DRAWINGS

FIGS. 5A and 5B are sets of image data generated to demonstrate an exemplary embodiment of the present invention;

FIG. 9 is a diagram of a system for generating an image of the top and entire periphery of an object and performing an inspection in accordance with an exemplary embodiment of the present invention;

DETAILED DESCRIPTION OF PREFERRED EMBODIMENTS

Figure 1:
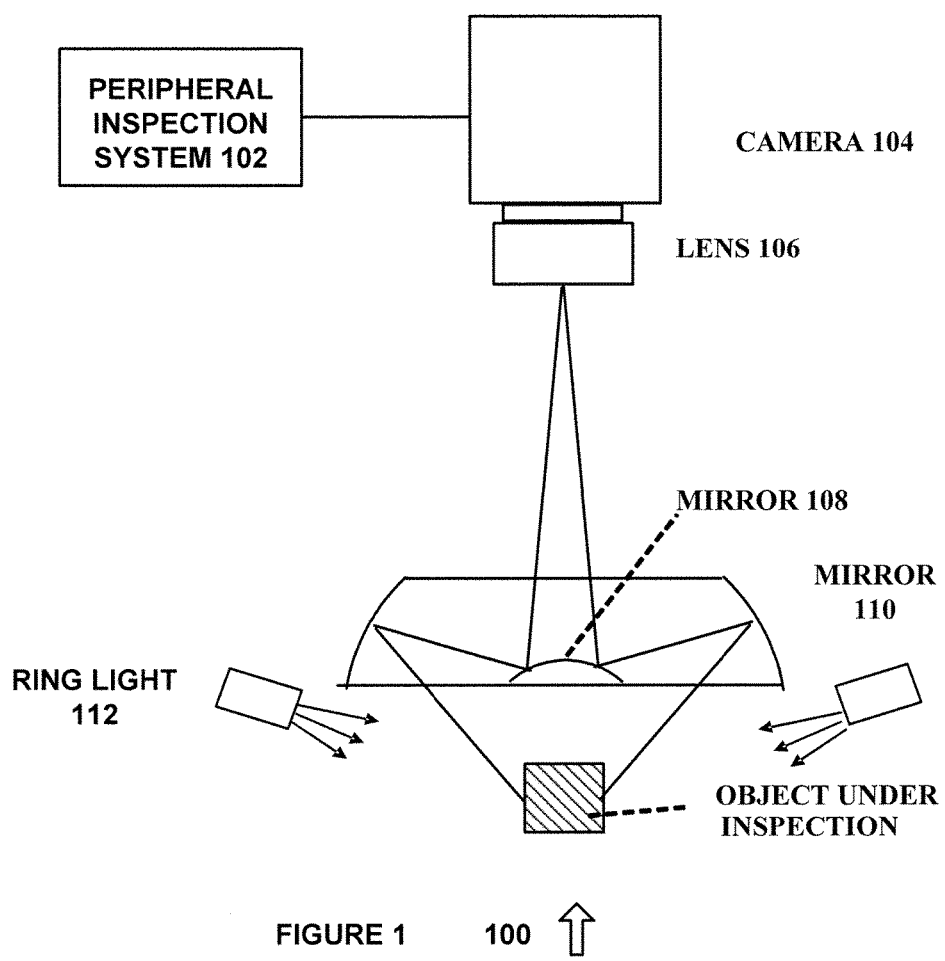
FIG. 1 is a diagram of a system for generating a single image of the entire periphery of an object and performing an inspection in accordance with an exemplary embodiment of the present invention.

In the description that follows, like parts are marked throughout the specification and drawings with the same reference numerals, respectively. The drawing figures might not be to scale, and certain components can be shown in generalized or schematic form and identified by commercial designations in the interest of clarity and conciseness.

FIG. 1 is a diagram of a system 100 for generating a single image of the entire periphery of an object and performing an inspection in accordance with an exemplary embodiment of the present invention. System 100 includes peripheral inspection system 102, which can be implemented in hardware, software, or a suitable combination of hardware and software, and which can one or more software systems operating on a general purpose processing platform.

As used herein, a hardware system can include a combination of discrete components, an integrated circuit, an application-specific integrated circuit, a field programmable gate array, or other suitable hardware. A software system can include one or more objects, agents, threads, lines of code, subroutines, separate software applications, two or more lines of code or other suitable software structures operating in two or more software applications or on two or more processors, or other suitable software structures. In one exemplary embodiment, a software system can include one or more lines of code or other suitable software structures operating in a general purpose software application, such as an operating system, and one or more lines of code or other suitable software structures operating in a specific purpose software application.

Peripheral inspection system 102 is coupled to camera 104. As used herein, the term "coupled" and its cognate terms such as "couples" or "couple," can include a physical connection (such as a wire, optical fiber, or a telecommunications medium), a virtual connection (such as through randomly assigned memory locations of a data memory device or a hypertext transfer protocol (HTTP) link), a logical connection (such as through one or more semiconductor devices in an integrated circuit), or other suitable connections.

Camera 104 generates image data of the periphery of an object under inspection. Lens 106 is used to focus light from mirror 108 onto an array of image sensors of camera 104. Mirror 108 is a spherical mirror section that receives image data from the periphery of the object under inspection from mirror 110. Mirror 110 is also a spherical mirror section that projects the periphery of the object under inspection onto mirror 108. Ring light 112 or other suitable lights illuminate the object under inspection.

In operation, the curvature of mirrors 108 and 110 are coordinated with the height of the object under inspection and the distance between mirror 108 and the object under inspection to allow a single image of the periphery of the object under inspection to be provided to camera 104. For example, the radius of curvature of mirror 110 and mirror 108 can be coordinated such that the object under inspection, when appropriately placed, can be seen from all sides from a single image generated at camera 104 from mirror 108 and lens 106. The radius of curvature of mirrors 108 and 110 and suitable distances can be calculated using general optics theory. In one exemplary embodiment of the present invention, the radius of the curvature of mirrors 108 and 110 are 13 mm and 31.3 mm, respectively. An aspherical profile of the mirrors 108 and 110 can be applied to reduce an image aberration.

In one exemplary embodiment, the image data generated by system 100 is polar projection data, where the distance between points around the periphery of the top of the object under inspection is less than the distance between points around the periphery of the bottom of the object under inspection. Peripheral inspection system 102 receives the image data of the object under inspection and identifies defects or other anomalies, such as by compensating for projection of the image of the object. In one exemplary embodiment, compensation is accomplished by performing conventional image data analysis (e.g. such as generation of a histogram of pixel brightness data) based on analysis of known defects in sets of projected image data. Likewise, identification of predetermined shapes within the projected image data can be performed based on a predetermined relationship between the object under inspection and the projected image data of that object. In one exemplary embodiment, compensation can include conversion of the image data from polar projection image data into a different coordinate format, or in other suitable manners.

Figure 2:
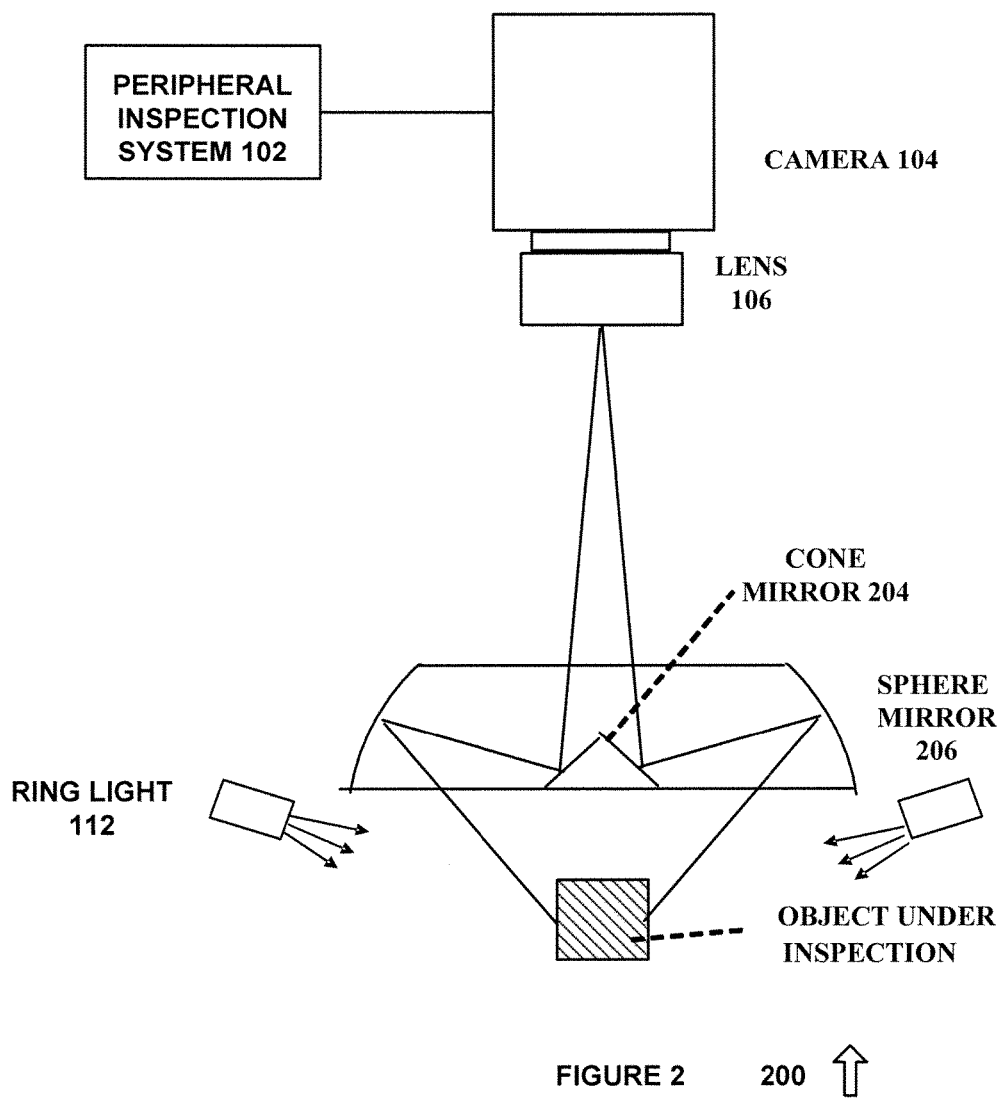
FIG. 2 is a diagram of a system for performing a peripheral inspection of an object in accordance with the present invention.

FIG. 2 is a diagram of a system 200 for performing a peripheral inspection of an object in accordance with the present invention. System 200 uses a cone mirror 204 in place of a spherical mirror 108.

As previously described, camera 104 generates image data of an image provided by the lens through the cone mirror 204. Spherical mirror 206 has a known spherical curvature and a radius that allows the polar projection image of the object under inspection that is generated by reflection of the image onto cone mirror 204 and generation into a set of image data by camera 104 to be inspected. The radius of curvature of mirrors 206 and angle of the cone 204 and suitable distances can be derived from general optics theory. An aspherical profile of the mirror 206 can be applied to reduce image aberration.

In operation, camera 104 generates a single set of image data for analysis by peripheral inspection system 102, such as to eliminate the need for generating multiple images of different sides of the object under inspection. The angle and size of cone mirror 204 is coordinated with the dimensions of spherical mirror 206 to allow a single set of polar projection image data of the periphery of an object under inspection to be generated.

Figure 3:
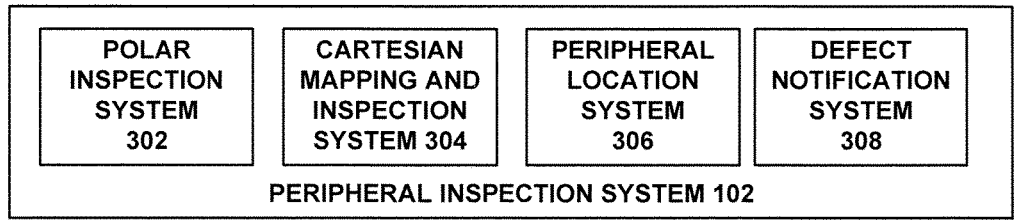
FIG. 3 is a diagram of a system for analyzing a single set of polar projection image data of an object under inspection in accordance with an exemplary embodiment of the present invention

FIG. 3 is a diagram of a system 300 for analyzing a single set of polar projection image data of an object under inspection in accordance with an exemplary embodiment of the present invention. System 300 includes peripheral inspection system 102, and polar inspection system 302, Cartesian mapping and inspection system 304, peripheral mapping location 306, and defect notification system 308, each of which can be implemented in hardware, software, or a suitable combination of hardware and software, and which can be one or more software systems operating on a general purpose processing platform.

Polar inspection system 302 receives image data that includes a polar projection of a circumferential view of an object under inspection. As previously described, such image data will typically be in polar projection format, such that items towards the center of the set of image data have a physical separation that is less than items towards the periphery of the set of image data. As such, polar inspection system 302 generates a set of image data to identify defects or other items that require an operator to be notified so that the object under inspection can be discarded or set aside for repair. Polar inspection system 302 can be used to identify predetermined metrics, such as a histogram or other statistical mapping of pixel brightness data, direct location procedures such as object mapping of known defect shapes, masking of predetermined sections of the image of the object that are not subject to inspection, indexing of features in the image data, or other suitable image inspection processes.

Cartesian mapping and inspection system 304 receives the image data in polar coordinate format and maps the polar coordinate image data to a Cartesian coordinate system. In one exemplary embodiment, the relationship between the location of individual pixels and the image data generated at those locations can be determined based on a mathematical relationship based on the dimensions of the set of mirrors that are used to generate the peripheral image data. In this manner, the polar projected image data can be mapped to a Cartesian coordinate system to allow image data inspection processes that require the use of Cartesian coordinate data to be utilized.

Peripheral location system 306 receives image data in a polar projection forma, Cartesian format, or other suitable formats, and locates one or more peripheral identifiers. In one exemplary embodiment, an object under inspection may have predetermined markings or features are identified by peripheral location system 306, to allow inspection of the object image data to be indexed. Likewise, peripheral location system 306 can use other suitable processes such as identifying external indexing features of equipment holding the object under inspection, generating histograms of pixel data for sections of the image data of the object under inspection data, locating text, applying masks, or other suitable processes. In one exemplary embodiment, peripheral location system 306 can generate error data in the event a peripheral orientation of the object under inspection can not be determined.

Defect notification system 308 receives inspection data from polar inspection system 302, Cartesian mapping and inspection system 304, peripheral location system 306, or other suitable systems and generates and defect notification data. In one exemplary environment, the defect notification data can cause an object under inspection to be extracted for further analysis, such as for manual inspection, to determine whether the object under inspection can be repaired, to determine whether the object must be discarded, or for other suitable purposes. Likewise, defect notification system 308 can generate control data to cause the object under inspection to be discarded by suitable mechanisms, such as where the object under inspection is a low cost part and the cost of repair is greater than the cost of disposal. Likewise, other suitable notification data can be generated by defect notification system 308.

In operation, system 300 allows peripheral image data of an object under inspection to be analyzed. Such peripheral image data is typically in a polar projection format, and may be mapped into a Cartesian system for inspection or can be inspected in its polar projection format. Indexing of features of the object under inspection may be required, and notification of an operator or generation of other control data for processing of potentially defective components can be performed by system 300.

Figure 4:
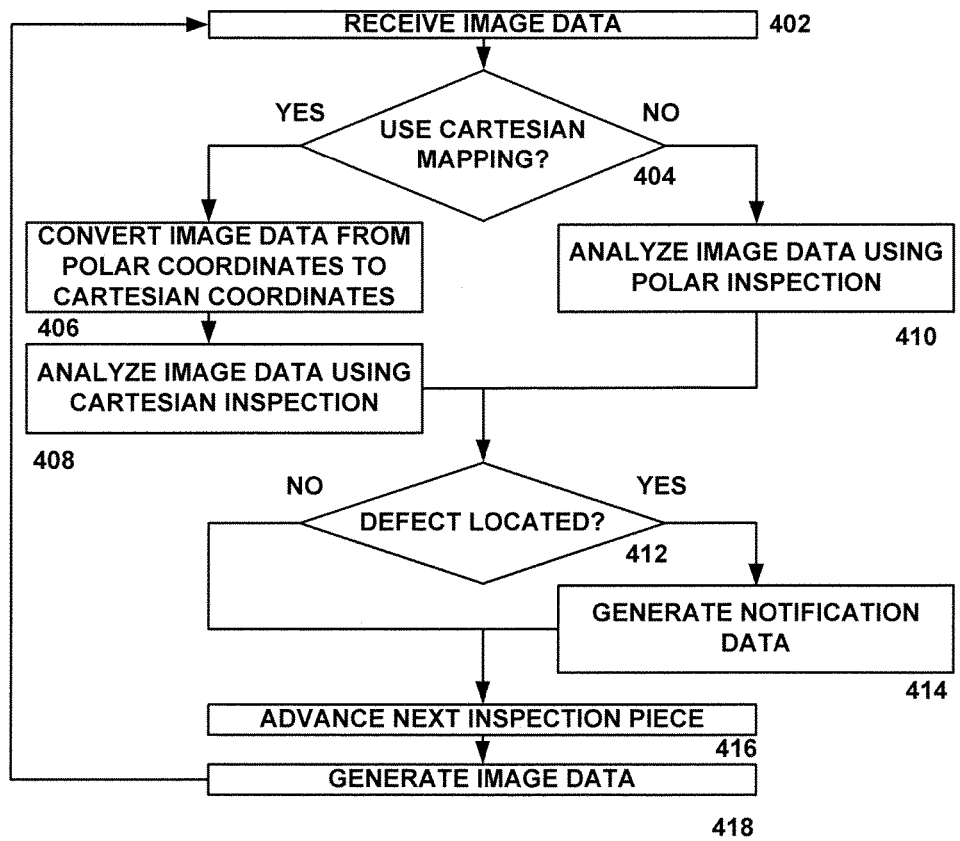
FIG. 4 is a flowchart of a method for processing peripheral image data in accordance with an exemplary environment of the present invention.

FIG. 4 is a flowchart of a method 400 for processing peripheral image data in accordance with an exemplary environment of the present invention. Method 400 begins are 402 where image data is received. In one exemplary environment, the image data can be polar projection data generated by an imaging lens 106 together with a spherical center mirror receiving peripheral image data of an object under inspection from and encircling mirror. Likewise, cone-shaped mirrors are other simple mirrors can be used. The method then proceeds to 404.

At 404, it is determined whether Cartesian mapping of the object under inspection is to be performed. In one exemplary embodiment, the image data can be generated in a polar projection format, such that mapping to Cartesian coordinates may be performed in order to perform inspection processes on the image data. If it is determined that Cartesian mapping is not to be performed, the method proceeds to 404 where the image data is analyzed using one or more polar projection inspection processes. In one exemplary embodiment, histograms or other suitable data can be used to analyze the pixels generated by the inspection image, identification of groups of pixels having predetermined characteristics can be performed, detection of projected text or other features can be used, or other suitable polar projected image data inspection methods can be applied. The method then proceeds to 412.

If it is determined that Cartesian mapping is to be performed at 404, the method proceeds to 406, where the image data is converted from polar projected data to Cartesian coordinate data. In one exemplary embodiment, the mathematical relationship between the object under inspection and mirrors that are used to project each side of the object under inspection into a single image can be used to map from the polar projection data to Cartesian coordinate data. Other suitable processes can also or alternatively be used. The method then proceeds to 408.

At 408, the mapped image data is analyzed using one or more Cartesian inspection processes. In one exemplary embodiment, the image data can be analyzed using histogram analysis, location of predetermined features or letters in the image data, indexing of the image data based on a map of features in the image data, blocking of areas from processing that are not under inspection, or other suitable processes.

At 412, it is determined whether a defect has been located. If no defect has been located, the method proceeds to 416, otherwise the method proceeds to 414 where notification data is generated. In one exemplary embodiment, notification data can include data that notifies an operator that a object under inspection needs to be checked for damage. Likewise, the notification data can include control data to a suitable device to remove the object under inspection. Likewise, other suitable notification data can be generated. The method then proceeds to 416.

At 416, the next inspection piece is advanced. In one exemplary embodiment, inspection can be formed "on the fly", such that advancement to the next inspection piece occurs in a continuous process. Likewise, the next inspection piece can be advanced upon completion of inspection of the current inspection piece, such as where the inspection piece is discarded upon generation of notification data. Likewise, other suitable processes can be used. The method then proceeds to 416.

At 416, image data of the new object under inspection is generated. In one exemplary embodiment, a single camera can be used to capture a projected peripheral image having projected polar coordinates. Likewise, other suitable processes can be used. The method then returns to 402.

In operation, method 400 allows a single set of image data to be analyzed that contains image data from all sides of an object under inspection. In one exemplary embodiment, mirrors can be used to generate a projected polar coordinate view of all sides of an object under inspection, such that image data generated is taken at a single spot so as to reduce the number of sets of image data that need to be generated. Likewise, other suitable processes can be used.

FIGS. 5A and 5B are sets of image data 500A and 500B generated to demonstrate an exemplary embodiment of the present invention. Image data set 500A shows a side view of a cylinder on which the words "Microview tech" have been inscribed. Image data set 500B shows a circumferential image of the sides of the cylinder. The image data set 500B was taken by system shown on FIG. 1. As can be seen from FIG. 5A, only the letters "Microv" are discernable from the flat side view presented to the image data generating device. In contrast, FIG. 58 shows the entire phrase "Microview tech," albeit in a projected polar coordinate system wherein the spacing of the image at the "top" of the letters is closer than the spacing of the image at the "bottom" of the letters. Furthermore, it can be observed that the letters "Microv" correspond to less than 50% of the information provided about the periphery of the cylinder, such that it would be necessary to take at least three side-on images of the cylinder to obtain all of the information from the periphery of the cylinder.

Furthermore, it is noted that the letters of "Microv" from the side-on image are themselves projected onto a cylinder, such that the spacing of the letters on the side of the cylinder is less than the spacing of the letters that directly face the image data generating device. As such, even if multiple sets of side-on image data were used, it might still be necessary to either convert that data from the cylinder projection plane to a Cartesian coordinate plane, or to take a larger number of sets of side-on image data such that the areas of the image data set where the areas having unacceptable variation due to projection onto a cylinder can be masked. As such, the present invention allows a single set of image data to be analyzed that provides a larger segment of the periphery of an object under inspection than side-on viewing, which reduces the number of sets of image data that must be generated and analyzed and increases the inspection speed of the system.

Figure 6:
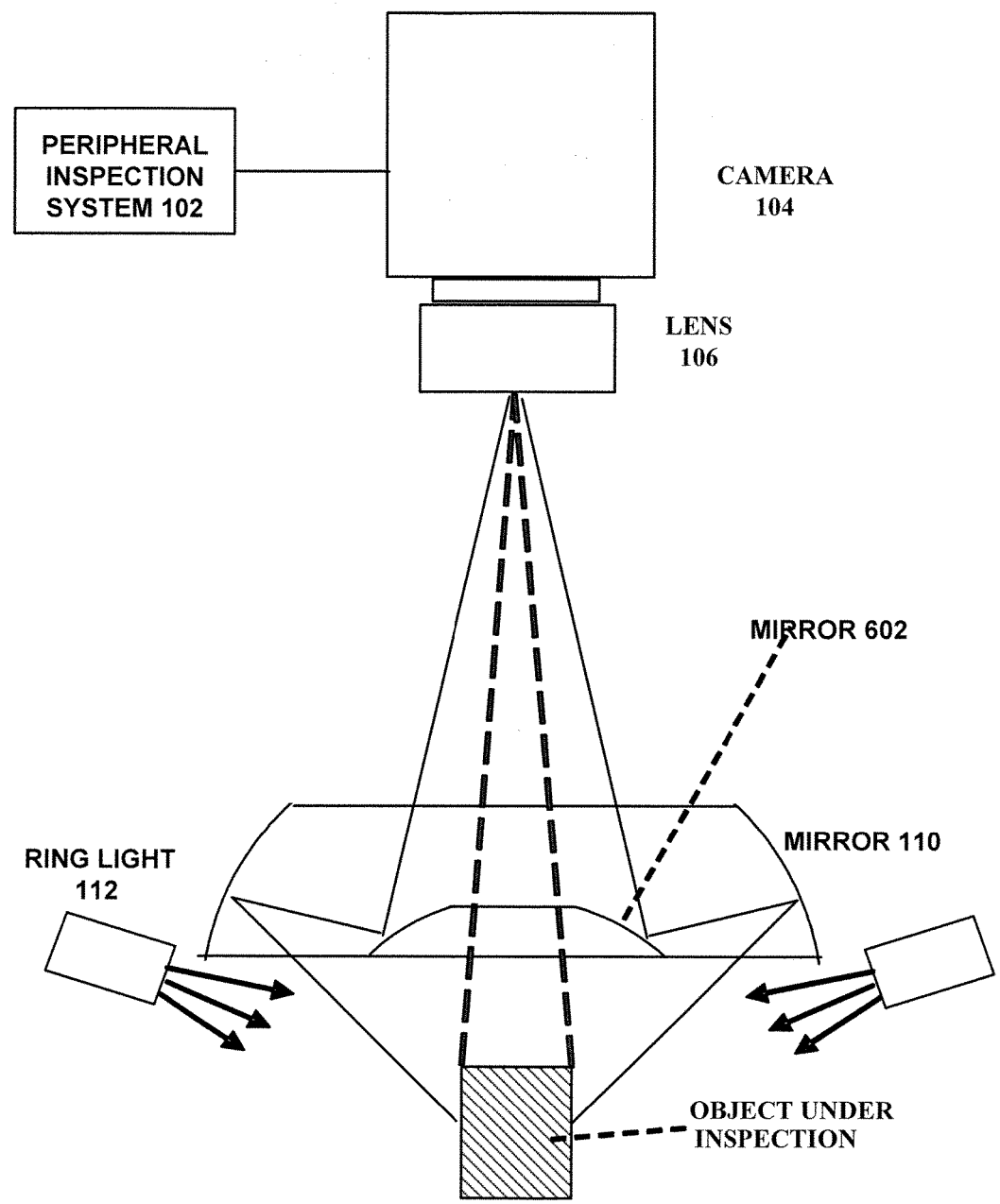
FIG. 6 is a diagram of a system for generating a single image of the top and the entire periphery of an object and performing an inspection in accordance with an exemplary embodiment of the present invention.

FIG. 6 is a diagram of a system 600 for generating a single image of the top and the entire periphery of an object and performing an inspection in accordance with an exemplary embodiment of the present invention. System 600 includes mirror 602 which is a spherical section mirror that has a center orifice to allow the top of the object under inspection to also be imaged.

Figure 7:
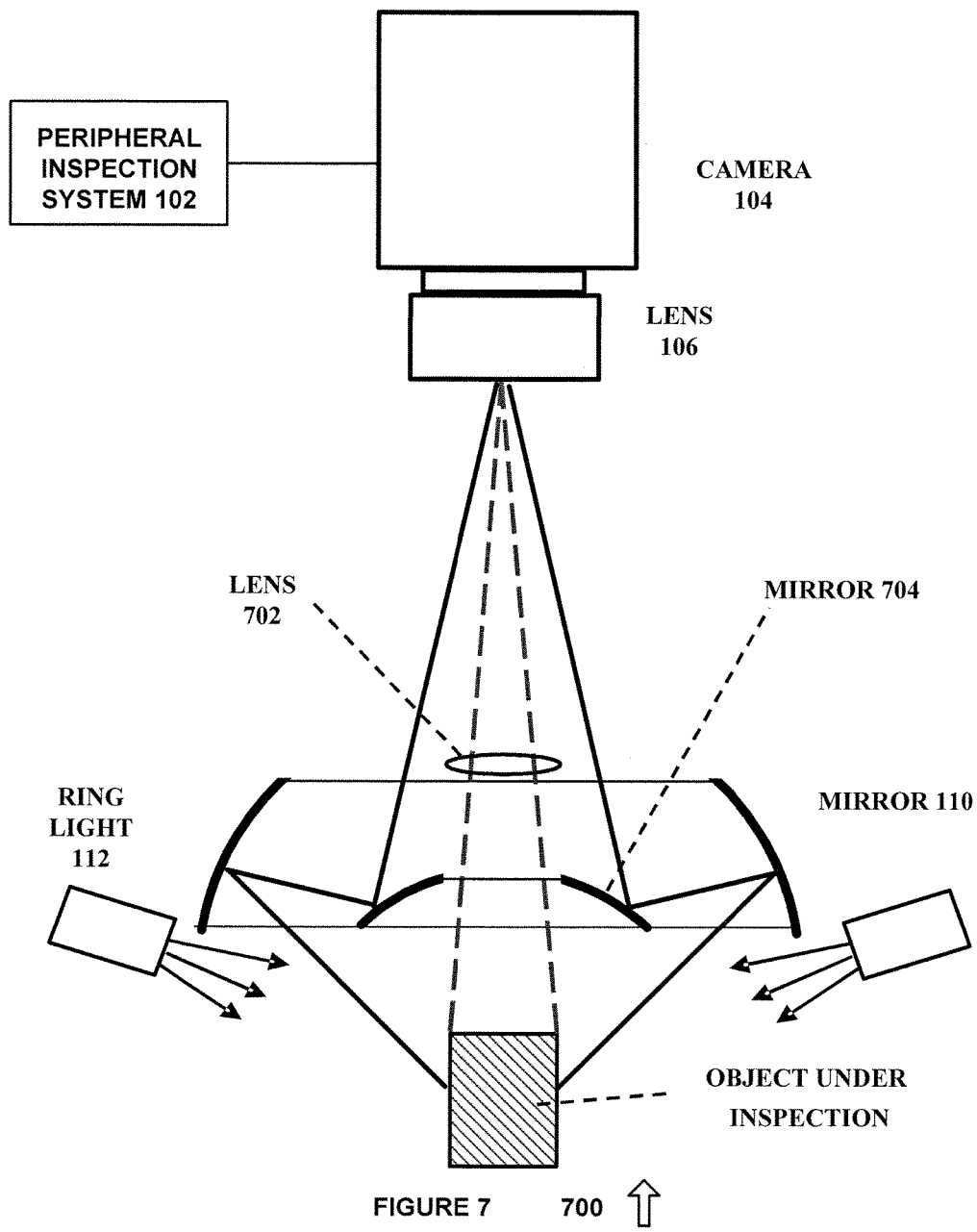
FIG. 7 is a diagram of a system for generating an image of the top and entire periphery of an object and performing an inspection in accordance with an exemplary embodiment of the present invention.

FIG. 7 is a diagram of a system 700 for generating an image of the top and entire periphery of an object and performing an inspection in accordance with an exemplary embodiment of the present invention. In addition to a spherical segment mirror 704, system 700 uses a lens 702 to focus the image on the top of the object under inspection. Lens 702 can be used to generate suitable magnification of the image of the top of the object at the same time.

Figure 8:
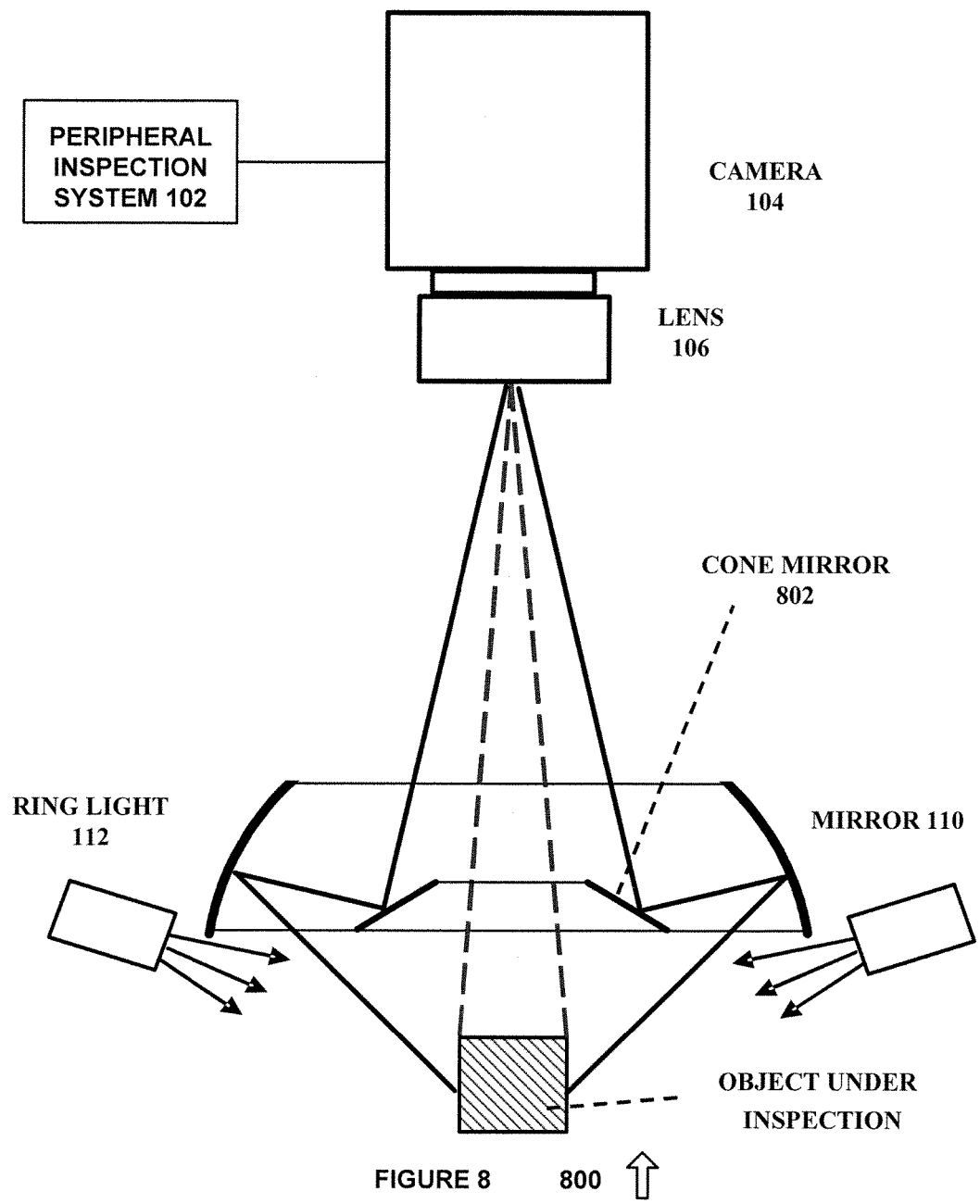
FIG. 8 is a diagram of a system for generating an image of the top and entire periphery of an object using a cone mirror in accordance with an exemplary embodiment of the present invention.

FIG. 8 is a diagram of a system 800 for generating an image of the top and entire periphery of an object using a cone mirror in accordance with an exemplary embodiment of the present invention. System 800 uses cone mirror 802 with a center orifice to allow the top of the object under inspection to also be imaged.

FIG. 9 is a diagram of a system 900 for generating an image of the top and entire periphery of an object and performing an inspection in accordance with an exemplary embodiment of the present invention. In addition to a conical segment mirror 902, system 900 uses additional lenses 904 to focus the image on of the top of the object under inspection. The lenses 904 can be used to generate suitable magnification of the image of the top of the object at the same time.

Figure 10A:
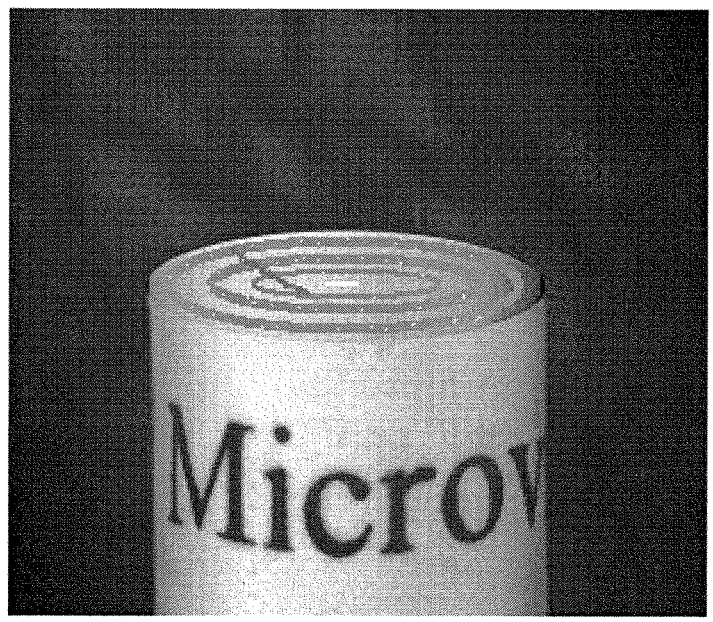
FIGS. 10A and 10B are sets of image data generated to demonstrate an exemplary embodiment for generating a single image of the top and the entire periphery of an object and performing an inspection.
Figure 10B:
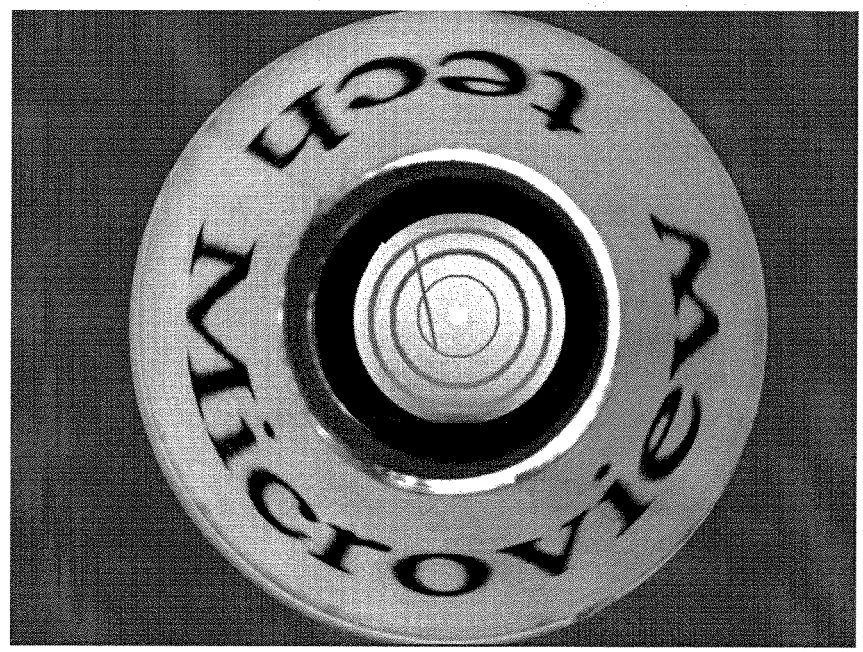

FIGS. 10A and 10B are sets of image data 1000A and 1000B generated to demonstrate an exemplary embodiment of the present invention. Image data set 1000B shows a circumferential image of the sides of the cylinder and top image at the center, such as might be obtained using system 700 or other suitable systems. In addition to the side markings of FIGS. 5A and 5B, FIGS. 10A and 10B include markings on the top of the object under inspection. As shown in FIG. 10A, these markings further require an image to be made of the top as well as of the sides of the object under inspection. As such, obtaining a single set of image data as shown in FIG. 10B further reduces the amount of image data that must be generated in order to perform an inspection of the object.

Figure 11:
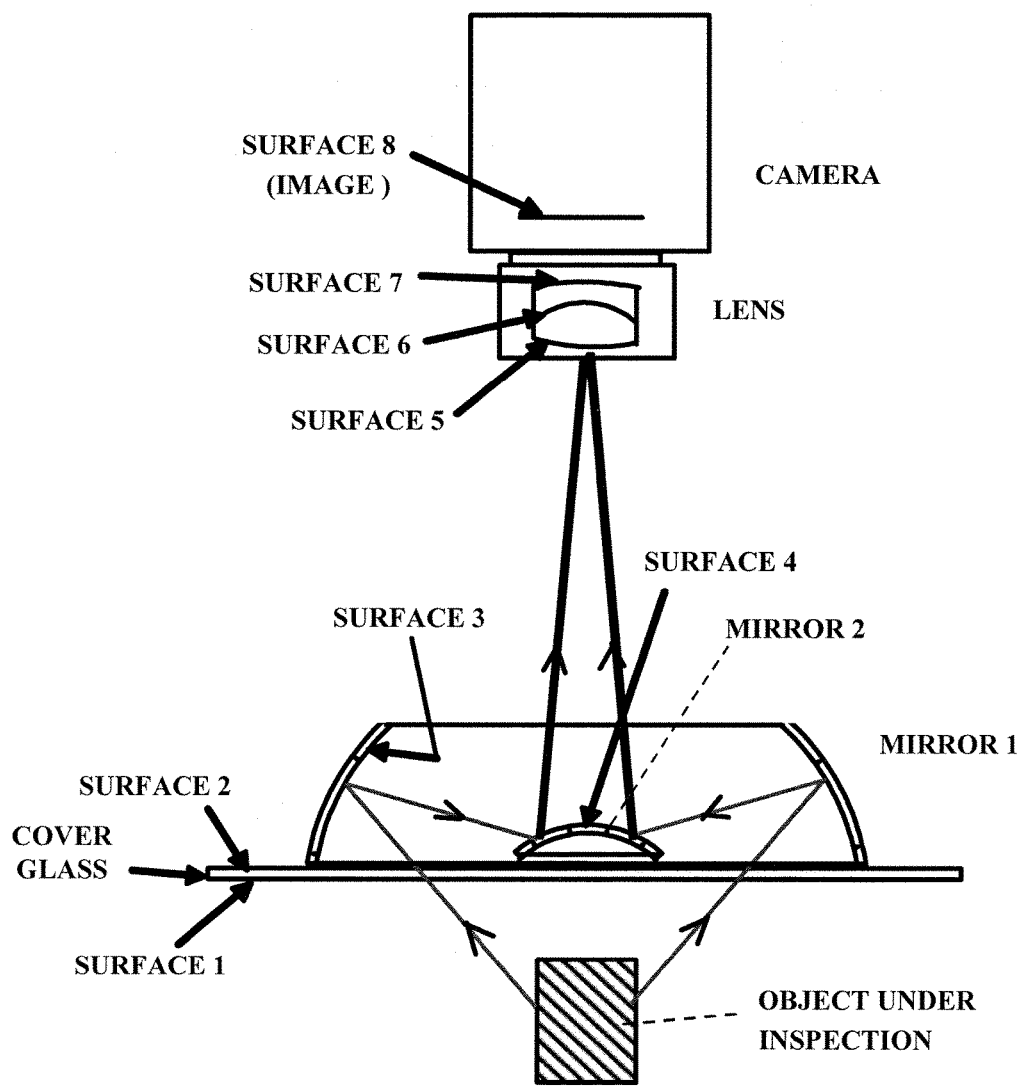
FIG. 11 is a diagram showing surfaces utilized herein.

FIG. 11 is a diagram showing surfaces utilized herein.

Exemplary Dimensions

Dimensions for one exemplary embodiment of the present invention are provided in Table 1:

TABLE 1

| Surface | Radius, mm | Thickness, mm | Diameter, mm | Schott Glass | Note |
|---|---|---|---|---|---|
| 1 | Infinity | 1.00 | 60 | BK7 | Cover glass |
| 2 | Infinity | 24.00 | 60 | — | |

TABLE 1-continued

| Surface | Radius, mm | Thickness, mm | Diameter, mm | Schott Glass | Note |
|---|---|---|---|---|---|
| 3 | −31.3 | −20.00 | 60 | Mirror (*) | Dmax = 60; Dmin = 32 |
| 4 | −13.0 | 84.67 | 18 | Mirror (**) | |
| 5 (stop) | — | 32.52 | 2.5 | — | Paraxial (***); F = 25 mm |
| 6 | Image | | | | |

Notes:
(*) Outer circumferential mirror. It has circular aperture: Dmax = 60 mm; Dmin = 32 mm.
(**) Inner spherical mirror
(***) Paraxial lens (F = 25 mm) is used. It can be replaced by real objective lens with focal lens 25 mm and aperture value F/#N = 8 up to F/#N = 16.

Dimensions for another exemplary embodiment of the present invention such as that shown in FIG. 11 that includes an object cylinder diameter range of 5 to 10 mm are provided in Table 2:

TABLE 2

| Surface | Radius, mm | Thickness, mm | Diameter, mm | Schott Glass | Note |
|---|---|---|---|---|---|
| 1 | Infinity | 1.00 | 60 | BK7 | Cover glass |
| 2 | Infinity | 24.00 | 60 | — | |
| 3 | −31.30 | −20.00 | 60 | Mirror (*) | Dmax = 60; Dmin = 32 |
| 4 | −13.00 | 84.67 | 18 | Mirror (**) | |
| 5 (stop) | 22.80 | 4.20 | 2.5 | BK7 | (***) |
| 6 | −8.40 | 1.50 | 3 | SF5 | |
| 7 | −18.06 | 32.00 | 3 | | |
| 8 | Image | | | | |

Notes:
(*) Outer circumferential mirror. It has circular aperture: Dmax = 60 mm; Dmin = 32 mm;
(**) Inner spherical mirror;
(***) Imaging lens (F = 25 mm) is doublet (surfaces 5, 6 & 7).

A camera such as model A102f from Basler AG company or other suitable cameras can be used to generate the image data.

Dimensions for one exemplary embodiment of the present invention that includes an object cylinder diameter range of 22 mm are provided in Table 3:

TABLE 3

| Surface | Radius, mm | Thickness, mm | Diameter, mm | Schott Glass | Note |
|---|---|---|---|---|---|
| 1 | Infinity | 3.00 | 120 | B270 | Cover glass |
| 2 | Infinity | 42.00 | 120 | — | |
| 3 | −60.00 | 31.3 | 114.6 | Mirror (*) | Dmax = 114.6; Dmin = 66 |
| 4 | −31.00 | 183.08 | 44 | Mirror (**) | |
| 5 (stop) | 22.80 | 4.20 | 2.5 | BK7 | (***) |
| 6 | −8.40 | 1.50 | 3 | Sf5 | |
| 7 | −18.06 | 32.00 | 3 | | |
| 8 | Image | | | | |

Notes:
(*) Outer circumferential mirror. It has circular aperture: Dmax = 114.6 mm; Dmin = 66 mm;
(**) Inner spherical mirror;
(***) Imaging lens (F = 25 mm) is doublet (surfaces 5, 6 & 7).

Dimensions for another embodiment of the present invention using a cone mirror and having an object cylinder diameter of 22 mm are provided in Table 4:

TABLE 4

| Surface | Radius, R, mm | Thickness, mm | Diameter, mm | Schott Glass | Conic, k | Note |
|---|---|---|---|---|---|---|
| 1 | Infinity | 3.00 | 96.0 | B270 | 0 | Cover glass |
| 2 | Infinity | 38.97 | 96.0 | — | 0 | |
| 3 | −48.14 | −22.20 | 94.6 | Mirror (*) | 0 | Dmax = 94.6; Dmin = 66 |
| 4 | −1E−19 | 98.77 | 30.0 | Mirror (***) | −2.26 | Cone angle 96°36′ |
| 5(stop) | 22.80 | 4.20 | 2.5 | BK7 | 0 | (**) |
| 6 | −8.40 | 1.50 | 3.0 | SF5 | 0 | |
| 7 | −18.06 | 30.27 | 3.0 | — | 0 | |
| 8 | Image | | | | | |

Notes:
(*) Outer circumferential mirror. It has circular aperture: Dmax = 114.6 mm; Dmin = 66 mm
(**) Imaging lens (F = 25 mm) is a doublet (surfaces 5, 6 & 7)
(***) Cone surface with top angle 96°36′

The "sag" or z-coordinate of the standard surface is given by:

$$z = \frac{cr^2}{1 + \sqrt{1 - (1+k)c^2 r^2}}$$

where:
c=1/R is the curvature (the reciprocal of the radius R)
r=radial coordinate in lens units and
k=conic constant.
The conic constant is less than −1 for hyperbolas, −1 for parabolas, between −1 and 0 for ellipses, 0 for spheres, and greater than 0 for oblate ellipsoids. The conic constant is less than 0 and the radius is 0<|R|<<1 for a cone surface.

Although exemplary embodiments of a system and method of the present invention have been described in detail herein, those skilled in the art will also recognize that various substitutions and modifications can be made to the systems and methods without departing from the scope and spirit of the appended claims.

What is claimed is:

1. A system for inspecting an object comprising:
an image data system configured to generate digital image data using a processor;
a first lens coupled to the image data system, wherein the first lens comprises a paraxial lens with a thickness of about 32 mm, a first surface with a diameter of about 2.5 mm and a focal length of about 25 mm;
a first circular mirror disposed between the first lens and at least a portion of a second circular mirror;
a ring light disposed between 1) the first circular mirror and the second circular mirror and 2) an object under inspection and configured to illuminate the object under inspection; and
a defect notification system configured to receive image data from a data memory in a polar projection format, to identify one or more defects in the image data using a processor and to generate notification data to alert an operator to perform additional manual inspection of an item associated with the image data in the polar projection format.

2. The system of claim 1 further comprising a second lens disposed between the first circular mirror and the first lens.

3. The system of claim 2 further comprising a third lens disposed between the ring light and the second circular mirror.

4. The system of claim 3 further comprising a cover glass disposed between 1) the object under inspection and 2) the first circular mirror and the second circular mirror.

5. The system of claim 1 wherein the first circular mirror comprises a diameter of about 60 mm and a radius of curvature of about −31 mm.

6. The system of claim 1 wherein the first circular mirror comprises a diameter of about 115 mm and a radius of curvature of about −60 mm.

7. The system of claim 1 wherein the first circular mirror comprises a diameter of about 95 mm and a radius of curvature of about −60 mm.

8. The system of claim 1 wherein the first lens comprises a paraxial lens with a thickness of about 32 mm, a first surface with a diameter of about 2.5 mm and a focal length of about 25 mm, and the first circular mirror comprises a diameter of about 60 mm and a radius of curvature of about −31 mm.

9. The system of claim 1 wherein the object has a cylindrical shape approximately 5 to 10 mm in diameter.

10. A system for inspecting an object comprising:
an image data system configured to generate digital image data using a processor;
a first lens coupled to the image data system wherein the first lens comprises a paraxial lens with a thickness, a first surface with a diameter and a focal length;
a first circular mirror disposed between the first lens and at least a portion of a second circular mirror;
a ring light disposed between 1) the first circular mirror and the second circular mirror and 2) an object under inspection and configured to illuminate the object under inspection; and
a defect notification system configured to receive image data from a data memory in a polar projection format, to identify one or more defects in the image data using a processor and to generate notification data to alert an operator to perform additional manual inspection of an item associated with the image data in the polar projection format.

11. The system of claim 10 wherein the first circular mirror comprises a diameter and a radius of curvature.

12. The system of claim 10 wherein the first circular mirror comprises a diameter.

13. A system for inspecting an object comprising:
an image data system configured to generate digital image data using a processor;
a first lens coupled to the image data system, wherein the first lens comprises a doublet having a first layer with a thickness of about 4.2 mm and a radius of curvature of about 23 mm, a second surface with a thickness of about 1.5 mm and a radius of curvature of about −8 mm, and a third surface with a thickness of about 30 mm and a radius of curvature of about −18 mm;
a first circular mirror disposed between the first lens and at least a portion of a second circular mirror;
a ring light disposed between 1) the first circular mirror and the second circular mirror and 2) an object under inspection and configured to illuminate the object under inspection; and
a defect notification system configured to receive image data from a data memory in a polar projection format, to identify one or more defects in the image data using a processor and to generate notification data to alert an operator to perform additional manual inspection of an item associated with the image data in the polar projection format.

14. The system of claim 13 wherein the first lens comprises a doublet having a first layer with a thickness of about 4.2 mm and a radius of curvature of about 23 mm, a second surface with a thickness of about 1.5 mm and a radius of curvature of about −8 mm, and a third surface with a thickness of about 30 mm and a radius of curvature of about −18 mm, and the first circular mirror comprises a diameter of about 60 mm and a radius of curvature of about −31 mm.

15. The system of claim 13 wherein the first lens comprises a doublet having a first layer with a thickness of about 4.2 mm and a radius of curvature of about 23 mm, a second surface with a thickness of about 1.5 mm and a radius of curvature of about −8 mm, and a third surface with a thickness of about 30 mm and a radius of curvature of about −18 mm, and the first circular mirror comprises a diameter of about 115 mm and a radius of curvature of about −60 mm.

16. The system of claim 15 wherein the object has a cylindrical shape approximately 20 mm in diameter.

17. The system of claim 16 further comprising a polar inspection system configured to receive image data at a processor that includes a polar projection of a circumferential view of an object under inspection and to apply predetermined pixel histogram metrics from a data memory to the polar projection of the circumferential view of the object under inspection to determine whether a defect is present in the image data.

18. The system of claim 16 further comprising a Cartesian mapping and inspection system configured to map polar coordinate image data to a Cartesian coordinate system using a processor to generate Cartesian image data and to apply predetermined pixel histogram metrics from a data memory to the Cartesian image data to determine whether a defect is present in the image data.

19. The system of claim 16 further comprising a peripheral location system configured to receive image data from a data memory in a polar projection format using a processor and to locate one or more peripheral identifier features in the image data to allow indexing of the image data for inspection.

20. The system of claim 13 wherein the first circular mirror comprises a diameter of about 60 mm and a radius of curvature of about −31 mm.

* * * * *